United States Patent

Martin et al.

[11] Patent Number: 5,847,128
[45] Date of Patent: Dec. 8, 1998

[54] WATER SOLUBLE DERIVATIVES OF CANNABINOIDS

[75] Inventors: Billy R. Martin, Richmond, Va.; Raj K. Razdan, Gloucester, Mass.

[73] Assignee: Virginia Commonwealth University, Richmond, Va.

[21] Appl. No.: 87,279

[22] Filed: May 29, 1998

[51] Int. Cl.$^6$ ............ A61K 31/533; C07D 413/12
[52] U.S. Cl. ................ 544/150; 514/232.8
[58] Field of Search .......... 544/150; 514/232.8

[56] References Cited

U.S. PATENT DOCUMENTS

| | | |
|---|---|---|
| 4,179,517 | 12/1979 | Mechoulam et al. |
| 4,327,028 | 4/1982 | Kaplan . |
| 4,876,276 | 10/1989 | Mechoulam et al. |
| 5,338,753 | 8/1994 | Burstein et al. |
| 5,389,375 | 2/1995 | ElShohly . |

OTHER PUBLICATIONS

Struwe, Annals of Pharm., 27, pp. 827–831, (1993).
AIDS Res. Hum. Retroviruses, 13(4), p. 305, 1997.
"Water–Soluble Derivatives of $\Delta^1$ –Tetrahydrocannabinol", Science, vol. 177, Aug. 1972.

Razdan et al., "Drugs Derived from Cannabinoids. 2$^{1a}$ Basic Esters of Nitrogen and Carbocyclic Analogs", Journal of Medicinal Chemistry, vol. 19, No. 4, 1976.

*Primary Examiner*—Robert W. Ramsuer
*Attorney, Agent, or Firm*—Whitham, Curtis & Whitham

[57] ABSTRACT

Water-soluble esters of tetrahydrocannabinoids, which are well-suited for administration in therapeutic aqueous formulations, having following general formula:

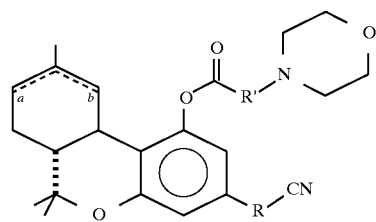

wherein a - - - b designates a 9(10) or a 9(8) double bond, R' is a —$(CH_2)_n$— linkage group where n is 1–8, and R is a -$(CZ_2)_n$- linkage group where n is 6 or more and Z independently is H or a substituent such as a lower alkyl group, and the pharmaceutically acceptable salts of these compounds.

9 Claims, No Drawings

WATER SOLUBLE DERIVATIVES OF CANNABINOIDS

FIELD OF THE INVENTION

The invention is generally related to water soluble derivatives of cannabinoids and their use in pharmaceutical administrations.

BACKGROUND OF THE INVENTION $\Delta^9$-tetrahydrocannabinol ($\Delta^9$-THC) [C.A. nomenclature], which alternatively is often referred to as "$\Delta^1$-THC" where terpene series nomenclature is used, is the primary active ingredient of the plant *Cannabis sativa* (marijuana). Occasionally small quantities of the $\Delta^8$-THC isomer of $\Delta^9$-THC are also present in the plant. Both of these THC compounds have known pronounced pharmacological effects on mammals including humans. A wide variety of therapeutic applications of these THC compounds have been proposed or investigated, e.g., treatment of glaucoma, high blood pressure, anxiety states, insomnia, allergy, asthma, epilepsy, nausea, vomiting, ulcers, anorexia, pain (including migraine), and so forth, such as reported in U.S. Pat. Nos. 4,179,517 and 5,389,375. However, the formulation of $\Delta^8$- or $\Delta^9$-THC for medicinal uses has been problematic in view of the fact that these THC compounds are resinous gum materials which are insoluble in water. On the other hand, known solvents for these THC compounds, such as polyethylene glycol, alcohol, and so forth, tend to have pharmacological activity of their own, which is undesired. As a consequence, previous efforts to formulate $\Delta^8$- or $\Delta^9$-THC for pharmacological testing has been frustrated.

As can be appreciated, there is a need for highly potent, water-soluble cannabinoid derivatives which allow for effective routes of administration.

SUMMARY OF THE INVENTION

The present invention relates to a new class of water-soluble esters of tetrahydrocannabinoids, which are of the following general formula I:

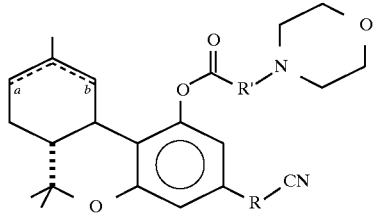

wherein a - - - b designates a 9(10) or a 9(8) double bond, R' is a —(CH$_2$)$_n$— linkage group where n is 1–8, and R is a -(CZ$_2$)$_n$- linkage group where n is 6 or more and Z independently is H or a substituent such as a lower alkyl group, and the pharmaceutically acceptable salts of these compounds.

In one particular embodiment, the present invention relates to the compound 3-(5'-cyano-1',1'-dimethylheptyl)-1-(4-N-morpholinobutyryloxy)-$\Delta^8$-THC, and the pharmaceutically acceptable salts of this compound.

The inventive formula I compounds have the advantage of being highly soluble in aqueous solvents and medium which makes the compounds suitable and attractive for pharmacological studies of the compounds. Accordingly, this invention also encompasses pharmaceutical compositions in which the formula I compounds are solubilized in an aqueous medium or carrier.

The inventive compounds of formula I can be administered in a wide variety of delivery routes including by inhalation (e.g., via aerosol delivery) for treatment of a wide variety of conditions including pain, asthma, nausea, and the AIDS wasting syndrome. The compounds also can be used in conjunction with analgesics such as morphine in pain control treatment.

DETAILED DESCRIPTION OF THE PREFERRED EMBODIMENTS OF THE INVENTION

In the present invention, water soluble derivatives of $\Delta^8$- or $\Delta^9$-tetrahydrocannabinol are provided without loss of the biologic activity of THC.

The pharmaceutically active compounds which are active ingredients of the novel pharmaceutical preparations are of the following general formula I:

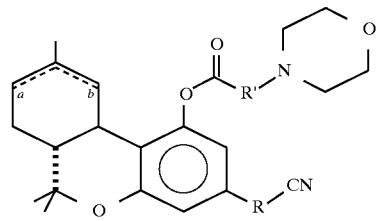

wherein a - - - b designates a 9(10) or a 9(8) double bond, wherein R' is an alkylene linkage group defined as —(CH$_2$)$_n$— where n is 1–8, and R is a substituted or unsubstituted alkylene linkage group defined as -(CZ$_2$)$_n$- where n is 6–12 or more and Z independently is H or a substituent such as a lower alkyl group (e.g., methyl), and the pharmaceutically acceptable salts of these compounds. In more specific embodiments, R is a 1',1'-dimethylheptylene or a 1',2'-dimethylheptylene group.

The pharmaceutically acceptable salts of the compounds of general formula I include those of the following general formula II:

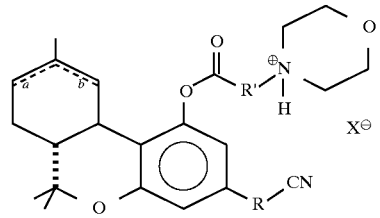

where X$^\ominus$ represents a negative charged ion such as, for example, chloride, bromide, iodide, nitrite, sulfite, phosphate, citrate, glutarate, acetate, perchlorate, ascorbate, tartrate, fumarate, maleate, lactate, or aspartate, and so forth, and a - - - b, R', and R have the same meanings as defined for general formula I.

Also, for purposes of general formulae I and II, it is to be understood that the $\Delta^8$- and $\Delta^9$-THC compounds generally can have methyl groups as substituents at the 6,6 and 9 positions. The compounds of formulae I and II are foams that are highly soluble in water, with water solubilities (at about 25° C.) of up to about 20 mg/mL, and more generally about 10 to about 20 mg/mL.

The C.A. numbering convention applicable to the THC derivative compounds described herein can be understood with reference to general formula III below:

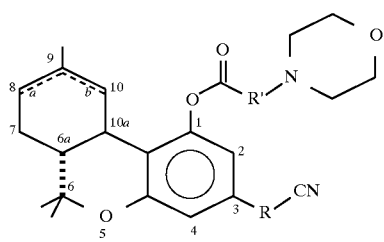

where a - - - b, R and R' have the same meanings as described hereinabove.

In synthesizing the compounds of the present invention, in general, cyano-functionalized-$\Delta^8$ (or $\Delta^9$)-THC is esterified with a carbodiimide compound as the condensing agent. The cyano-functionalized-$\Delta^8$ (or $\Delta^9$)-THC reactant for this esterification reaction can be prepared by reacting 5'-bromo-1',1-dimethylheptyl-$\Delta^8$-THC with an alkali cyanide, e.g., sodium cyanide, in an aprotic solvent, such as dimethylsulfoxide (DMSO), at about 50° C. for several hours (e.g., about 3 hours). Then, the presence of the phenolic hydroxyl group in the cyano-functionalized tetrahydrocannabinoid is exploited to prepare various basic esters thereof having a water solubility suitable for pharmacological testing and usage of these compounds.

In one non-limiting representative implementation, morpholinobutyral esters of cyano-functionalized tetrahydrocannabinoids are prepared having requisite water solubility for pharmacological testing and usage. This has been achieved by preparing morpholinobutyral esters bearing a nitrogen moiety of cyano-functionalized $\Delta^8$- or $\Delta^9$-(THC) with the use of dicyclohexylcarbodiimide as the condensing agent. The provision of water-soluble THC derivatives in this manner allows for pharmacological studies and therapeutic uses to be performed.

The compounds of the present invention can be used in therapeutic applications including, for example, treatment of pain (including migraines), asthma, nausea, and the AIDS wasting syndrome. For example, in the relief and prevention of pain in a host or patient, the method comprises administering to a host or patient an amount of a compound selected from the general formulae I or II which are set forth hereinabove that is effective for providing some degree of analgesic effect. The compounds of the above described formulae I and II can be employed in a free base form or in a salt form as indicated.

The pharmaceutical composition also can include pharmaceutically acceptable additives or adjuncts, such as antoxidants, free radical scavenging agents, buffering agents, steroids, and so forth, to the extent that they do not hinder or interfere with the therapeutic effect desired of the compounds.

The manner in which the compounds can be administered can vary. The compounds can be administered by inhalation (e.g., aerosol form); orally (e.g., in aqueous form within a pharmaceutically acceptable aqueous solution); parenterally, such as intravenously (e.g., within an aqueous saline solution or aqueous dextrose solution) or as an infusion or injection (e.g., as a suspension or as an emulsion in a pharmaceutically acceptable aqueous solution or mixture of aqueous liquids); transdermally (e.g., using a transdermal patch); or using an enema. Again, an important attribute of the THC derivatives of this invention is that they can be conveniently and effectively administered to a host in aqueous-based solutions, suspensions, or emulsions, in view of their enhanced water solubility property. The aqueous medium used as the solvent for the solute THC derivative compounds of the present invention can be based solely on water as the liquid medium. Alternatively, conventional organic solvents (e.g., alcohols, glycerine, polyethylene glycol and so forth) also could be present in minor amounts as admixed with the primary water medium, but only to the extent they do not have pharmacological activity. Again, water is the preferred medium for solubilizing the active THC derivative compounds because of its absence of pharmacological activity and convenience of use.

The compounds described herein in the practice of the inventive therapeutic method can be administered via aerosol delivery via an atomized aqueous medium.

The administration of pharmaceutical compositions of the present invention can be intermittent, or at a gradual, or continuous, constant or controlled rate to a warm-blooded animal. In addition, the time of day and the number of times per day that the pharmaceutical formulation is administered can vary.

When used as an analgesic, the dose of the compound is that amount effective to prevent occurrence of the symptoms of pain or to treat some symptoms of pain, or other form of physical discomfort (e.g., nausea), from which the patient suffers. By "effective amount", "therapeutic amount" or "effective dose" it is meant that amount sufficient to elicit the desired pharmacological or therapeutic effects; for example, thus resulting in effective analgesia.

The host or patient for the therapeutic treatment using the compounds described herein generally are mammalian, such as rodents, monkeys, dogs and humans.

The effective dose can vary, depending upon factors such as the condition, size and age of the patient, the severity of the symptoms being treated, and the manner in which the pharmaceutical composition is administered. For human patients, the effective dose of the compounds of the hereinabove described formulae generally requires, for oral administration, a dosage range amount of about 0.1 to about 25 mg/24 hr./patient, and more specifically about 1 to about 10 mg/24 hr./patient. Preferably, the dosage is divided up into several equal smaller dosages administered at regular time intervals over each 24 hr. period. The oral administration can be accomplished using aqueous pharmacological solutions, suspensions, emulsions, syrups, elixirs, and so forth, which have the THC derivative active agents solubilized therein. In rodents, such as mice, the effective dosage of the analgesic compound, as administered orally, can be characterized as ranging from about 1 mg active agent/kg host to about 15 mg active agent/kg host. In rodents, such as mice, the effective dosage of the analgesic compound, as administered parenterally (e.g., intravenous injection), can be characterized as ranging from about 0.01 mg active agent/kg host to about 0.1 mg active agent/kg host.

In the following examples, objects and advantages of this invention are further illustrated by various embodiments thereof but the details of those examples should not be construed to unduly limit this invention. All parts and percentages therein are by weight unless otherwise indicated.

EXAMPLES

Example 1

The compound 3-(5'-cyano-1',1'-dimethylheptyl)-1-(4-N-morpholinobutyryloxy)-$\Delta^8$-THC.HCl was synthesized in the following manner.

A. Synthesis of 5'-cyano-1',1'-dimethylheptyl-$\Delta^8$-THC intermediate.

An intermediate, 5'-cyano-1',1'-dimethylheptyl-Δ$^8$-THC (1), was first synthesized according to the following related schematic (Reaction Scheme 1) and its related descriptions herein. The described reactants and products encountered in the synthesis of the intermediate compound 5'-cyano-1',1'-dimethylheptyl-Δ$^8$-THC are cross-referenced with parenthetical numbering to the reaction scheme 1 provided below.

Reaction Scheme 1:

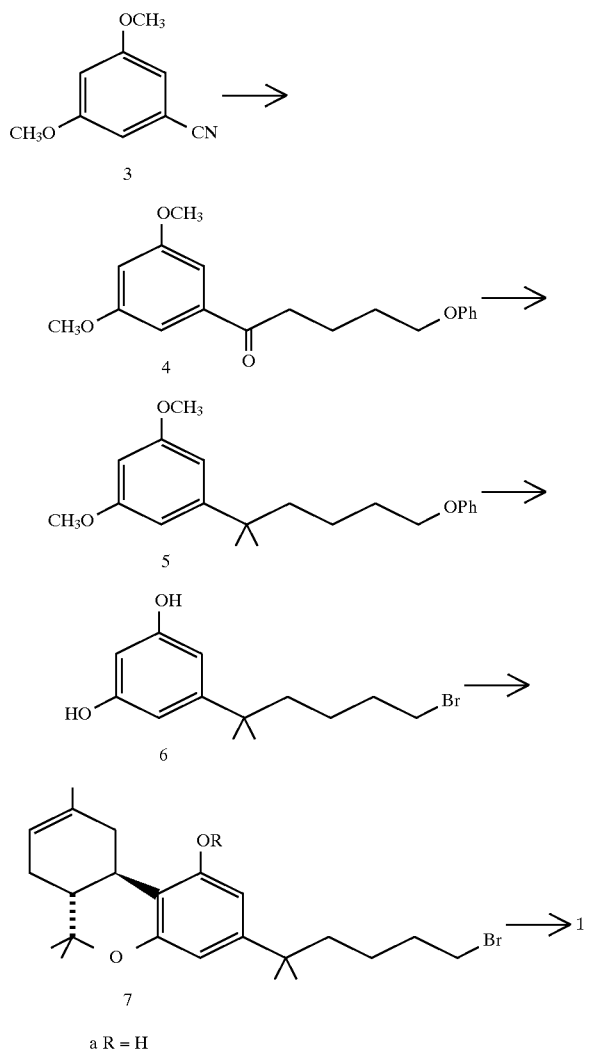

a R = H

Compound 5'-cyano-1',1'-dimethylheptyl-Δ$^8$-THC (1) was synthesized starting with commercially available 3,5-dimethoxybenzonitrile (3) according to the synthesis pathway shown in Reaction Scheme 1.

As an overview of Reaction Scheme 1, a Grignard reagent prepared from 4-bromophenoxybutane in tetrahydrofuran (THF) was treated with the nitrile compound (3) to produce the ketone compound (4) (85% yield), which, on further treatment, with diemthyl zinc and TiCl$_4$ in CH$_2$Cl$_2$ at −40° C. gave the resorcinal compound (5)(63% yield). Demethylation and replacement of the phenoxy group by bromine with the BBr$_3$ in CH$_2$Cl$_2$ at 5° C. produced compound (6)(85% yield), followed by condensation with p-menth-2-ene-1,8-diol in the presence of p-toluenesulfonic acid and refluxing in benzene, to form the Δ$^8$-tetrahydrocannabinol (THC) analog compound (7a) (41% yield). Treatment of compound (7a) with sodium cyanide in DMSO produced the intermediate compound 5'-cyano-1',1'-dimethylheptyl-Δ$^8$-THC compound (1) in 76% yield.

i. Synthesis of Compound (4)

Now in more specific terms, the synthesis of 1-phenoxy-5-(3,5-dimethoxyphenyl)pentane (4) was accomplished as follows. To a mechanically stirred Grignard reagent (prepared from 91.6 g, 0.4 mmol of 4-bromophenoxybutane and 14.6 g, 0.6 mmol of magnesium turnings in 400 mL of anhydrous THF), added 48.9 g, 0.3 mmol of 3,5-dimethoxybenzonitrile (3) all at once and heated to reflux for 3 hours. The reaction was cooled to 0° C. with an ice bath for 15 minutes followed by the slow addition of 6N HCL (150 mL), and then allowed to stir at reflux overnight. The THF was removed in vacuo and the residue dissolved in ethyl acetate (300 mL) and 6N HCL (50 mL). The layers were separated and the aqueous fraction extracted with ethyl acetate (4×150 mL). The combined ethyl acetate extract was washed with saturated NaHCO$_3$, followed by water and brine. After drying, it was concentrated and the residue was chromatographed on silica gel (650 g), eluting with 5%–25% ether/hexanes, to yield 79.8 g (85%) of compound (4). The product was compound (4) as confirmed by NMR analysis.

ii. Synthesis of Compound (5)

The synthesis of 1-phenoxy-5-(3,5-dimethoxyphenyl)-5,5-dimethylpentane (5) was accomplished as follows. In a dry three-necked flask equipped with a mechanical stirrer, a thermometer and an addition funnel, was added anhydrous CH$_2$Cl$_2$ (300 mL) and cooled to −40° C. A 1M solution of TiCl$_4$ in CH$_2$Cl$_2$ (382 mL, 0.382 mmol) was transferred to the addition funnel (cannula) and added slowly to the cold CH$_2$Cl$_2$ solution maintaining a temperature of −40° C. After the addition, the solution was cooled to −50° C. and via the addition funnel, a 2M solution of dimethyl zinc in toluene (191 mL, 0.191 mmol) was added as rapidly as possible, maintaining the mixture temperature between −40° C. to −50° C. Upon complete addition, the viscous red suspension was stirred vigorously for 10 minutes after which a solution of compound 4 (20 g, 63.6 mmol) in dry CH$_2$Cl$_2$ (50 mL) was added rapidly maintaining the temperature between −40° C. to −50° C. The bright orange mixture was stirred vigorously for 2 hours at −45° C. to −35° C., and then the temperature was allowed to rise slowly to −10° C. over 2 hours with continued stirring. The mixture was poured onto ice water (0° C.) (600 mL) and the aqueous layer was extracted with CH$_2$Cl$_2$ (4×200 mL). The combined CH$_2$Cl$_2$ extract was washed with brine (200 mL), dried and concentrated, and the residue was chromatographed on silica gel (500 g), eluting with 1.5%–30% ethyl acetate/hexanes, to give 13.7 g (63% yield) of compound 5. The product was compound (5) as confirmed by NMR analysis.

iii. Synthesis of Compound (6)

The synthesis of 5'-bromo-1',1'-dimethyl-3,5-benzenediol was accomplished as follows.

A solution of compound (5) (10 g, 30 mmol) in benzene (100 mL) was azeotroped for 2.5 hours. After cooling to 5° C., a 1M solution of boron tribromide in CH$_2$Cl$_2$ (70 mL, 70 mmol) was added dropwise via an addition funnel over 20 minutes and stirred overnight at 23° C. The mixture was poured onto ice water (500 mL) and the aqueous layer was extracted with ether (5×200 ml). The combined ether extract was washed with 5% Na$_2$SO$_3$ solution(300 mL), followed by water (2×300 mL), brine (200 mL), and then dried and concentrated in vacuo. The viscous residue was chromatographed on silica gel 9300 g), eluting with 20% and then by 50% ether/hexanes mixture to yield 7.47 g (85% yield) of the resorcinal compound (6). The product was compound (6) as confirmed by NMR analysis.

iv. Synthesis of Compound (7a)

The synthesis of 5'-bromo-1',1'-dimethylheptyl-$\Delta^8$-tetracannabinol was accomplished as follows.

Compound (7a) was prepared by condensing the resorcinal compound (6) (6.13 g, 21.3 mmol) with p-menth-2-ene-1,8-diol (5.7 g, 33.4 mmol) in the presence of p-toluenesulfonic acid (0.13 g, 0.68 mmol) and refluxing in benzene (1.2 L). The gum obtained after work up was chromatographed on silica gel (600 g), eluting with 30% ethyl acetate/hexanes to yield 3.72 g (41% yield) of compound (7a). The product was compound (7a) as confirmed by NMR analysis.

v. Synthesis of Compound (1)

The synthesis of 5'-cyano-1',1'-dimethyl-$\Delta^8$-tetrocannabinol was accomplished as follows.

To a warm solution(50° C.) of compound (7a) (2.9 g, 6.8 mmol) in DMSO (55 mL) added NaCN (1.2 g, 24.5 mmol) and stirred at 50° C. for 3 hours. The solvent was removed in vacuo and the residue was treated with water and extracted with ether. The combined ether extract was washed with brine, dried and concentrated and the residue was chromatographed on silica gel (80 g). Elution with 30% ether/hexanes gave 1.90 g (76% yield). The product was compound (1) as confirmed by NMR analysis.

B. Synthesis of 3-(5'-cyano-1',1'-dimethylheptyl)-1-(4-N-morpholinobutyryloxy)-$\Delta^8$-THC.HCl active agent.

To a solution of 5'-cyano-1',1'-dimethylheptyl-$\Delta^8$-THC (1) (0.10 g, 0.28 mmol), as synthesized as described above, and 4-morpholinobutyric acid hydrochloride (0.08 g, 0.42 mmol) in CH$_2$Cl$_2$ (7 mL), was added 1,3-dicyclohexylcarbodiimide (0.09 g, 0.44 mmol). The reaction was stirred under N$_2$ overnight (approximately 12 hrs.) at room temperature (approximately 25° C.). The reaction was cooled in an ice bath and the white precipitate was filtered. The reaction scheme used for converting the 5'-cyano-1',1'-dimethylheptyl-$\Delta^8$-THC into the basic ester is schematically shown below in Scheme 2:

Reaction Scheme 2:

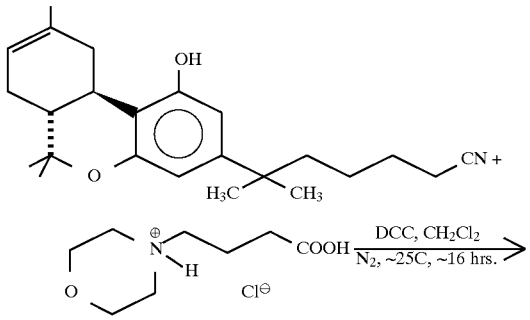

-continued

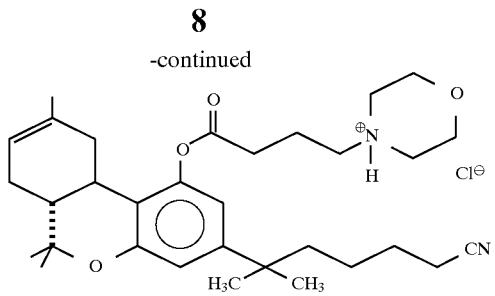

After removal of the solvent in vacuo, the reaction residue was taken up in a solution of CH$_2$Cl$_2$ (0.75 mL) and cyclohexane (3.75 mL) and placed in the freezer overnight under N$_2$. The solution was filtered cold and the flask was washed with a 5/1 mixture of CH$_2$Cl$_2$ and cyclohexane (6 mL). The solvent was removed in vacuo. The residue was taken up in saturated NaHCO$_3$ (20 ml) and extracted with CH$_2$Cl$_2$ (3×15 mL). The organic extracts were checked for neutral pH and washed with brine (2×10 ml). The organic extracts were dried (MgSO$_4$) and the solvent was removed in vacuo. The crude ester was purified by flash chromatography (10 g SiO$_2$, 20% ethyl acetate/hexanes, then 50% ethyl acetate/hexanes) to give the product as a partial solid. The free base (0.12 g) was dissolved in ether (2 ml) and etheral HCl (0.33 mL, 1M sol.) was added and stirred for 30 minutes at room temperature. The solvent was removed in vacuo, followed by adding ether to the residue and evaporating it in vacuo. This was repeated using CH$_2$Cl$_2$ and then ether to give the product as a pale yellow foam. Yield was 0.11 g (70%) and the product was 3-(5'-cyano-1',1'-dimethylheptyl)-1-(4-N-morpholinobutyryloxy)-$\Delta^8$-THC as confirmed by NMR analysis ($^1$H NMR (CDCl$_3$)$\delta$ 1.10 (s, 3H, C(6)-gem-CH$_3$), 1.19–1.81 (m,10H,aliphatic H, —N—CH$_2$—CH$_2$—),1.25 (s,6H, C(1')-gem-CH$_3$), 1.39 (s, 3H, C(6)-gem-CH$_3$), 1.69 (s, 3H, C(11) —CH$_3$), 2.00–3.73 (m, 6H, —CH$_2$—COO, C(6a)H, C(10a)H, C(10)H$_2$), 4.00–4.30 (m, 10H, —N—(CH$_2$)$_3$—, —CH$_2$—O—CH$_2$), 5.45 (br d, 1H, vinylic H), 6.49 (d, 1H, J=1.8 Hz, aromatic H), 6.68 (d, 1H, J=1.8 Hz, aromatic H); Anal. (C$_{32}$H$_{47}$N$_2$O$_4$Cl·0.7 H$_2$O), Calc. C, 67.22; H, 8.53; N, 4.90, Found C, 67.00; H, 8.54; N, 4.99).

Example 2

Animal studies were performed to investigate the analgesic effects of the 3-(5'-cyano-1',1'-dimethylheptyl)-1-(4-N-morpholinobutyryloxy)-$\Delta^8$-THC.HCl active agent as synthesized in Example 1.

As to the experimental protocol, male ICR mice were injected intravenously with an aqueous solution of the drug at concentrations indicated below, and the animals were tested 15 minutes later for tail-flick responses. The aqueous medium used was 100% sterile water. The active agent was completely soluble in the water medium.

The protocol of the tail-flick test was as follows. The apparatus that was used for the tail-flick test contained a light source placed directly above a photocell connected to a timer. The mouse was held under a cloth by the technician conducting the experiment. The tail of the test animal was placed over the photocell and the light was turned on. When the test animal felt the discomfort of the heat from the light, it was freely able to remove its tail from the lamp. The photocell than sensed that the tail had moved and the timer was stopped. The typical nontreatment reaction time for an animal subjected to this test was about 2–4 seconds. This test involved a spinal reflex action similar to the removal of a finger from a hot stove. In treated animals, the latency to remove the tail lengthens in proportion to the analgesic potency of the drug. No animal was allowed to remain under the lamp for greater than 10 seconds to prevent any burns to the tail. No animal was subjected twice to this test.

Upon performing the tail-flick tests in manner described above, the drug was found to produce analgesia with an ED50 (i.e., a dose that produces 50% of the maximal possible effect) of 0.02 mg/kg.

The drug was also observed to be effective when it was administered orally in an aqueous solution (100% sterile water medium) to male ICR mice. A dose of 3 mg/kg that was administered orally to male ICR mice produced maximal analgesia within 30 minutes and the effect subsided by 4 hours.

An oral dose of 10 mg/kg in male ICR mice produced 100% analgesia effect at one hour and the effects were long lasting. At 6 hours after this administration of the active agent, there was still 30% analgesia observed in the treated animals.

While the invention has been described in terms of its preferred embodiments, those skilled in the art will recognize that the invention can be practiced with modification within the spirit and scope of the appended claims.

What is claimed is:

1. A compound of the formula

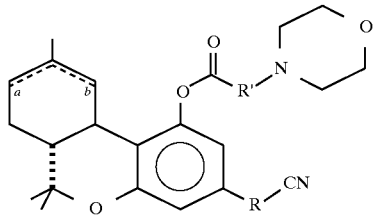

wherein a - - - b designates a 9(10) or a 9(8) double bond, R' is a —(CH$_2$)$_n$— linkage group where n is 1–8, and R is a -(CZ$_2$)$_n$- linkage group where n is 6 or more and Z independently is H or a lower alkyl group, and pharmaceutically acceptable salts thereof.

2. 3-(5'-cyano-1',1'-dimethylheptyl)-1-(4-N-morpholinobutyryloxy)-Δ$^8$-tetrahyrocannabinol, and pharmaceutically acceptable salts thereof.

3. A pharmaceutical composition comprising a compound solubilized in an aqueous medium, wherein said compound is of the formula

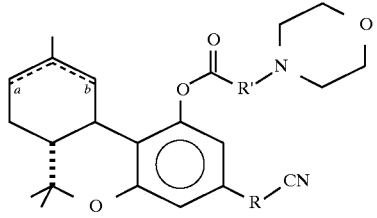

wherein a - - - b designates a 9(10) or a 9(8) double bond, R' is a —(CH$_2$)$_n$— linkage group where n is 1–8, and R is a -(CZ$_2$)$_n$- linkage group where n is 6 or more and Z independently is H or a lower alkyl group, and pharmaceutically acceptable salts thereof.

4. The pharmaceutical composition of claim 3, wherein said aqueous medium is selected from the group consisting of pure water, an aqueous emulsion, an aqueous suspension, an atomized aqueous solution, an aqueous elixir, and an aqueous syrup.

5. A method of relieving pain in a mammal comprising administering to said mammal an effective analgesic amount of a pharmaceutical composition containing a compound solubilized in an aqueous medium, wherein said compound is of the formula

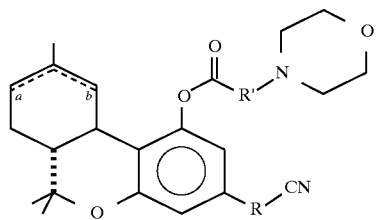

wherein a - - - b designates a 9(10) or a 9(8) double bond, R' is a —(CH$_2$)$_n$— linkage group where n is 1–8, and R is a -(CZ$_2$)$_n$- linkage group where n is 6 or more and Z independently is H or a lower alkyl group, and pharmaceutically acceptable salts thereof.

6. The method of claim 5 wherein said step of administration is performed by aerosol delivery.

7. The method of claim 5 wherein said step of administration is performed by oral administration.

8. The method of claim 5 wherein said step of administration is performed parenterally.

9. A method of treating asthma, nausea, or the AIDS wasting syndrome in a human comprising administering to said human an effective therapeutic amount of a pharmaceutical composition containing a compound solubilized in an aqueous medium, wherein said compound is of the formula

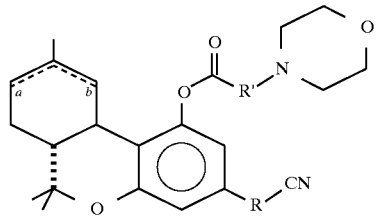

wherein a - - - b designates a 9(10) or a 9(8) double bond, R' is a —(CH$_2$)$_n$— linkage group where n is 1–8, and R is a -(CZ$_2$)$_n$- linkage group where n is 6 or more and Z independently is H or a lower alkyl group, and pharmaceutically acceptable salts thereof.

* * * * *

UNITED STATES PATENT AND TRADEMARK OFFICE
CERTIFICATE OF CORRECTION

PATENT NO.   : 5,847,128
DATED        : December 8, 1998
INVENTOR(S)  : Martin et al.

It is certified that error appears in the above-identified patent and that said Letters Patent is hereby corrected as shown below:

Column 1,
Line 53, delete "6" and insert --5--;
Line 58, delete "dimethylheptyl" and insert --dimethylpentyl--;

Column 2,
Line 36, delete "dimethylheptylene" and insert --dimethylpentylene--;

Column 3,
Line 19, delete "dimethylheptyl" and insert --dimethylpentyl--;

Column 4,
Line 62, delete "dimethylheptyl" and insert --dimethylpentyl--;
Line 66, delete "dimethylheptyl" and insert --dimethylpentyl--;

Column 5,
Line 1, delete "dimethylheptyl" and insert --dimethylpentyl--;
Line 6, delete "dimethylheptyl" and insert --dimethylpentyl--;
Line 51, delete "dimethylheptyl" and insert --dimethylpentyl--;

Column 6,
Line 1, delete "dimethylheptyl" and insert --dimethylpentyl--;
Line 56, delete "dimethylheptyl" and insert --dimethylpentyl--;

Column 7,
Line 2, delete "9300g)" and insert -(300g)-;
Line 10, delete "dimethylheptyl" and insert --dimethylpentyl--;
Line 25, delete "dimethyl" and insert --dimethylpentyl--;
Line 37, delete "dimethylheptyl" and insert --dimethylpentyl--;
Line 40, delete "dimethylheptyl" and insert --dimethylpentyl--;
Line 50, delete "dimethylheptyl" and insert --dimethylpentyl--;

UNITED STATES PATENT AND TRADEMARK OFFICE
CERTIFICATE OF CORRECTION

PATENT NO. : 5,847,128
DATED : December 8, 1998
INVENTOR(S) : Martin et al.

It is certified that error appears in the above-identified patent and that said Letters Patent is hereby corrected as shown below:

Column 8,
Line 32, delete "dimethylheptyl" and insert --dimethylpentyl--;
Line 46, delete "dimethylheptyl" and insert --dimethylpentyl--;

Column 9, Claim 1,
Line 38, delete "6" and insert --5--;

Column 9, Claim 2,
Line 41, delete "dimethylheptyl" and insert --dimethylpentyl--;

Column 10, Claim 3,
Line 1, delete "6" and insert --5--;

Column 10, Claim 5,
Line 27, delete "6" and insert --5--; and

Column 10, Claim 9,
Line 55, delete "6" and insert --5--.

Signed and Sealed this

Third Day of July, 2001

*Attest:*

*Attesting Officer*

NICHOLAS P. GODICI
*Acting Director of the United States Patent and Trademark Office*